US007206625B2

(12) United States Patent
Kurtz et al.

(10) Patent No.: US 7,206,625 B2
(45) Date of Patent: Apr. 17, 2007

(54) METHOD AND APPARATUS FOR THE COLLECTION OF PHYSIOLOGICAL ELECTRICAL POTENTIALS

(75) Inventors: Isaac Z. Kurtz, Toronto (CA); Yuri Sokolov, Mississauga (CA)

(73) Assignee: Vivosonic Inc., Toronto, Ontario ( * ) Notice: Subject to any disclaimer, the term of this patent is extended or adjusted under 35 U.S.C. 154(b) by 87 days.

(21) Appl. No.: 10/690,630

(22) Filed: Oct. 23, 2003

(65) Prior Publication Data

US 2005/0090727 A1    Apr. 28, 2005

(51) Int. Cl.
*A61B 5/04*    (2006.01)
(52) U.S. Cl. ...................... 600/372; 600/383
(58) Field of Classification Search ................ 600/372, 600/383
See application file for complete search history.

(56) References Cited

U.S. PATENT DOCUMENTS

| | | | | |
|---|---|---|---|---|
| 3,559,193 A | * | 1/1971 | Savaglio | 600/508 |
| 3,565,060 A | * | 2/1971 | Sipple | 600/508 |
| 3,628,527 A | * | 12/1971 | West | 600/372 |
| 3,896,790 A | * | 7/1975 | Dikmen | 600/383 |
| 4,263,561 A | | 4/1981 | Weber | 330/149 |
| 5,038,782 A | * | 8/1991 | Gevins et al. | 600/383 |
| 5,279,305 A | | 1/1994 | Zimmerman et al. | |
| 5,368,041 A | | 11/1994 | Shambroom | |
| 5,501,230 A | * | 3/1996 | Laribiere | 600/508 |
| 6,381,481 B1 | * | 4/2002 | Levendowski et al. | 600/383 |
| 6,428,484 B1 | * | 8/2002 | Battmer et al. | 600/554 |
| 6,597,942 B1 | | 7/2003 | Yonce | 600/509 |
| 2001/0029327 A1 | * | 10/2001 | Eloranta et al. | 600/372 |
| 2004/0073104 A1 | * | 4/2004 | Brun del Re et al. | 600/372 |
| 2004/0254435 A1 | * | 12/2004 | Mathews et al. | 600/372 |

FOREIGN PATENT DOCUMENTS

WO    WO 03/073929 A1    12/2003

OTHER PUBLICATIONS

Ferree, T.C. et al., Scalp Electrode Impedance, Infection Risk, and EEG Data Quality, Clinical Neurophysiology, vol. 112, Issue 3, Mar. 2001, pp. 536-544.
Metting VanRijn, A.C. et al., Low-Cost Active Electrode Improves the Resolution in Biopotential Recordings, 18th Annual International Conference of the IEEE Engineering in Medicine and Biology Society, 1996, pp. 101-102.
Canadian Intellectual Property Office, Written Opinion, Mar. 7, 2005, pp. 1-5.
Canadian Intellectual Property Office, International Search Report, Mar. 7, 2005, pp. 1-3.
Bonmassar et al., SAR Computations in a Realistic and High-Resolution Model of the Head with EEG Electrodes in Place, Neuroimage, vol. 16, Issue 2, Suppl. 1, Abstr. 73, May 2002.

* cited by examiner

*Primary Examiner*—Lee S. Cohen

(57) ABSTRACT

An invention is disclosed that provides an apparatus, method and system for the collection of physiological electrical potential signals. In one embodiment, the apparatus comprises integrating amplifier and an electrode into a combined unit for attaching or affixing to a subject (e.g., an animal or a human). Resulting from the extremely small or short connection between the conductive portion of the electrode and the amplifier, significantly less noise is introduced into the signal detected by the amplifier. The amplifier thus amplifies a signal with a much higher signal-to-noise ratio as compared with conventional electrode to lead wire to amplifier arrangements.

28 Claims, 4 Drawing Sheets

METHOD AND APPARATUS FOR THE COLLECTION OF PHYSIOLOGICAL ELECTRICAL POTENTIALS

FIELD OF THE INVENTION

This invention relates to physiological electrical potentials and, more particularly, to a method and device for the collection of these electrical potentials.

BACKGROUND

Living animals generate electrical potentials which, when collected, detected and analysed, can be used for a variety of purposes. For example, synchronous neural activity in a live animal or human brain produces electrical potentials that can be detected at the surface of the scalp with conductive electrodes. These detected potentials can then be used in a wide variety of clinical applications, particularly diagnostic applications.

It is known to collect these electrical potentials generated by living animals through the application of passive electrodes applied to the skin of the animal. These electrodes consist of a conductive surface or pad that is coupled or adhered to the skin of a subject. The operation of the conductive pad is often facilitated by the additional application of a conductive substance, such as gel, between the skin and the electrode. The conductive pad of the electrode is connected to a lead wire which, in turn, is electrically coupled to an amplifier. The length of the lead wire is typically in excess of 1 m (usually from approximately 1 m to 2.5 m) and electrically connects the amplifier (housed in a signal processing device) and the electrode. The amplifier amplifies the difference in electric potentials between a signal electrode and a reference electrode, both of which are affixed to the subject (human or animal). The amplifier is typically housed together with some signal processing device which, typically, is also adapted to record and analyse any detected electrical potentials which have been amplified by the amplifier. Unfortunately, this known arrangement of the electrode, lead wire and amplifier has significant shortcomings, particularly for the following reasons.

Unlike typically well known electrical potentials in common use in other industries and other areas of activity, the electrical potentials generated by living animals are often very small in amplitude—often in the millivolt, microvolt, or even nanovolt range. As a result, these electrical potentials are easily "drowned out" or lost due to noise from the electrical potentials generated by other items in the vicinity of the subject (e.g., lighting, the signal processing device, other equipment, etc.). That is, the differential electric potentials of interest in most applications (often smaller than 1 microvolt) are usually smaller than the electrical noise that is detected by the amplifier when no signal is present.

Significant sources of electrical noise which will often be detected by the amplifier are caused by the plurality of time-varying and time-invariant electromagnetic fields that are often present in a test environment where the electrode-lead wire-amplifier arrangement is employed. These time varying electromagnetic fields are inductively and capacitively coupled to the lead wire that carries the signal from the electrode to the amplifier. Consequently, these time varying electromagnetic fields introduce noise onto the lead wire that will be detected and amplified by the amplifier. A second significant source of noise is motion artefacts; i.e., the noise induced in the lead wire as it moves through a static (i.e., time-invariant) electromagnetic field.

To address these known shortcomings, efforts have been made to shorten the lead wire in an attempt to reduce noise. However, these efforts have had limited success. Amongst the problems with these efforts is that it is impractical in many applications to tether a subject (whether it is an animal or human) with a wire that is less than about 1 meter long to the amplifier.

Another measure to reduce noise that has had some success, albeit limited, is achieved with differential measurements since common mode noise, i.e. noise that is identically present in two wires, can be cancelled to a certain degree. Unfortunately, not all of the noise induced by the various electromagnetic fields is identical in both signal wires and, thus, some significant amount of noise will still be not cancelled and thus present in the recording system.

Additional efforts to reduce the effect of noise include conducting multiple tests and then averaging the results of these multiple tests. Unfortunately, conducting repeated tests in an attempt to eliminate or reduce any noise detected has the unwanted effect of significantly lengthening the testing process. Since it is often preferred that the subject remain still or, in some cases, unconscious, a lengthening of the testing process is quite undesirable especially when the test subject is a young child or animal.

Another shortcoming with the known electrode-based systems of measuring electrical potentials is the difficulty in determining whether the electrodes have been properly attached or affixed to the subject (e.g., animal or human), while proper attachment, as typically indicated by low electrical impedance between the electrodes, is crucial for the recorded signal-to-noise ratio. As a result, significant care must be taken by the clinician to properly attach these electrodes and then carefully monitor any potentials measured to assess whether the measurements are indicative of improper electrode attachment. If a clinician or other operator is of the opinion that at least one of the electrodes is improperly attached to the subject, a time consuming review of each electrode is necessary to determine which electrode is improperly attached to the subject. To overcome this time consuming process some clinical systems include impedance detection, i.e., a means for automatically detecting if an electrode is poorly connected with the skin of a subject. The accepted method of impedance detection (see for example U.S. Pat. No. 5,368,041) is to introduce a small-current signal to each electrode. The voltage from each electrode to ground is measured and is proportional to the impedance of the electrode. However, such an impedance-detection system requires additional circuitry and the introduction of another electrical current. This additional current and circuitry will be a further source of noise in any signal detected. Moreover, the additional circuitry increases the costs and complexity of the overall system.

Accordingly, a method and apparatus for the collection of electrical potentials which addresses, at least in part, some of the above-noted shortcomings is desired.

SUMMARY OF THE INVENTION

In one aspect of the invention there is provided an apparatus comprising an integrated amplifier and electrode into a combined unit for attaching or affixing to a subject (e.g., an animal or a human). Resulting from the extremely small or short connection between the conductive portion of an electrode and the amplifier, significantly less noise is introduced into the signal detected by the amplifier. The amplifier thus amplifies a signal with a much higher signalto-noise ratio as compared with conventional electrode to lead wire to amplifier arrangements.

In an alternate embodiment of the invention, an impedance detection method and apparatus is provided that may be used whenever an amplifier with bipolar transistor inputs is used to detect the signal (i.e., the electrical potential generated by the subject). Bipolar transistor amplifiers, by their nature, introduce an input bias current into each of the differential signal inputs. These bias currents are an inherent property of the bipolar transistor inputs and result in an offset at the amplifier output that is proportional to the difference in impedance between the input leads. The polarity or phase of the common-mode signal can be used to determine which electrode contact is faulty, thus reducing the time-consuming and painstaking process that afflicts current electrode arrangements.

This method is ideally suited for applications where the signal of interest is a differential signal and advantageously requires no additional circuitry to generate, filter, and detect the impedance signal. Hence, it reduces the cost, size, complexity, and total noise of the system with compared current arrangements. A further advantage of these impedance-detection method and apparatus is that it is particularly well suited for use in a small space, the type of physical environment in which electrodes are often employed.

A further aspect of the invention provides a method and an apparatus comprising mounting at least two signal electrodes to a subject and at least one reference electrode. The at least one reference electrode comprises a differential amplifier directly connected the conductive portion of the at least one reference electrode. The at least two electrodes are each electrically connected to the differential amplifier of the at least one reference electrode via wires with the lengths close to the distances between the connected electrodes.

As will be apparent to those of ordinary skill in the art, the methods and apparatus achieve artefact noise reduction in at least three ways. First, at least one lead wire, a significant source of wire-induced noise, is eliminated completely. Second, the remaining lead wires may be as short as allowed by the size of the area of interest on the subject (e.g., the distance between wires mounted to the subject's head) which is typically much shorter than the typical one-meter length (or greater) used in known arrangements and systems. Third, motion artefacts are significantly reduced since all lead wires, electrodes and the amplifier are each mounted to the subject and all move together significantly reducing differential movement and hence differential artefact noise that otherwise would be induced in the lead wires due to motion through environmental electromagnetic fields.

A further aspect of the invention comprises wireless transmission of the electrical potentials amplified by the electrode-mounted amplifier(s) to a signal-processing device. In this aspect of the invention, the invention further comprises electronic circuitry which transforms the amplified electrical potentials into radio waves and transmits them to a remote radio receiver.

In a still further aspect of the invention, the wireless transmission of the electrical potentials comprises performing some signal processing enabling wireless transmission of a digital representation of the amplified electrical potentials. A signal processing device is then adapted to receive and use the digital representation of the amplified electrical potentials transmitted from the subject.

In a still further aspect of the invention, an amplifier and related circuitry comprise an integrated circuit affixed to an electrode that employs chip-on-board technology enabling the integrated circuit to be directly mounted to the conductive pad or a small printed circuit board (PCB). This arrangement results in a significantly smaller packaging than conventional packaging (e.g., Small Outline Integrated Circuit (SOIC), etc.). The integrated circuit and its associated lead wires electrically connected to the PCB may be encapsulated for its protection, for example in an epoxy resin.

In one aspect of the present invention there is provided an electrode module for affixing to a subject to assist in measuring electrical potentials in said subject, said electrode module comprising an amplifier component mounted directly to an electrode.

In a further aspect of the invention there is provided a method of amplifying electrical potentials in a subject, said method comprising amplifying a differential electrical potential signal received from first and second signal electrodes, said amplifying is performed near or on one of said signal electrodes and a reference electrode.

In a still further aspect of the invention there is provided a system for measuring electrical potentials in a subject, said system comprising a pair of electrodes electrically coupled to an amplifier mounted to a reference electrode, said reference electrode comprising a conductive pad electrically connected to said amplifier, said amplifier for amplifying a differential electrical signal detected by said pair of electrodes.

These as well as other novel advantages, details, embodiments, features and objects of the present invention will be apparent to those skilled in the art from following the detailed description of the invention, the attached claims and accompanying drawings, listed herein, which are useful in explaining the invention.

BRIEF DESCRIPTION OF THE DRAWINGS

In the following text and drawings, wherein similar reference numerals denote similar elements throughout the several views thereof, the present invention is explained with reference to illustrative embodiments, in which.

DETAILED DESCRIPTION OF THE PREFERRED EMBODIMENTS

In the described embodiments of the present invention, reference is made to the subject from which electrical potentials are being detected, measured and analysed. The subject illustrated in some of the figures is illustrated as the head of a human. It is to be noted that other subject areas (i.e., other portions of a human) or other animals could equally be a subject for which the current invention could be employed to detect electrical potentials.

Figure 1:
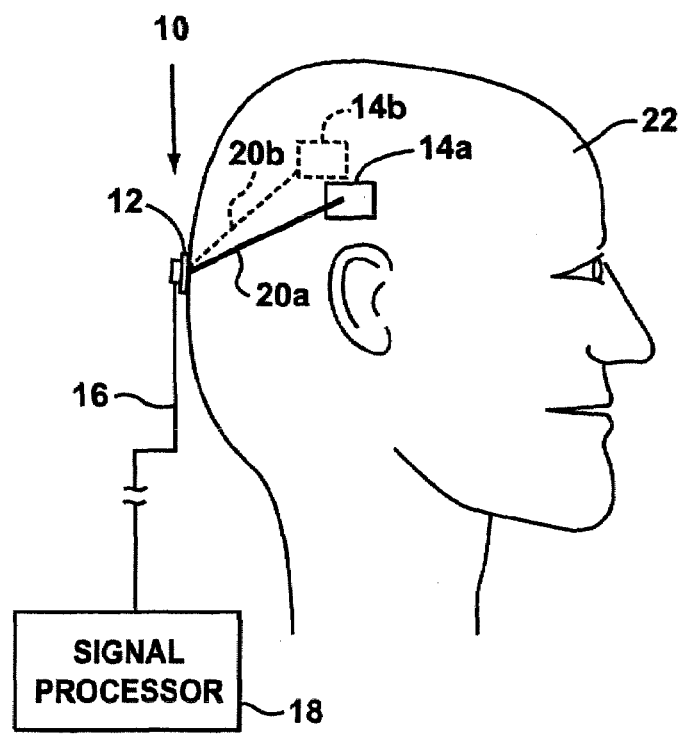
FIG. 1 is a side view schematic diagram depicting an embodiment of the invention affixed to a subject's (human's) head.

Referencing FIG. 1, an electrical potential system 10 is illustrated. Electrical potential system 10 includes a reference electrode module 12 (which, as is described below includes an amplifier component 38, not shown in FIG. 1) electrically coupled to two or more conventional electrodes 14. In FIG. 1, two signal electrodes 14 (also referred to herein as simply "electrodes 14") are illustrated—a first electrode 14a is illustrated in the foreground while a second electrode 14b (shown in dotted line) is in the background. Electrodes 14a, 14b are electrically coupled to reference electrode module 12 by lead wires 20a, 20b, respectively.

Reference electrode module 12 is also electrically coupled to signal processing device 18 by way of connector 16.

Reference electrode module 12 and electrodes 14 are affixed or mounted to subject 22 through known adhesives or other fixation methods or mechanisms. Additionally, a conductive substance such as electrode gel, for example, may be used to enhance or ensure electrical conduction between the skin of subject 22 and electrodes 12, 14.

Lead wires 20a and 20b are preferably selected to be taut when electrodes 12 and 14 have been affixed to subject 22. When lead wires 20a, 20b are taut the chance of differential motion artefacts resulting from lead wire 20a moving in a manner different from lead wire 20b is significantly reduced.

Connector 16 is preferably a conventional shielded wire allowing amplified electrical potential signals to be transmitted from reference electrode module 12 to signal-processing device 18.

Signal-processing device 18 operates to receive and process signals received from reference electrode module 12 via connector 16. As will be apparent from the description below, signal-processing device 18 is a conventional signal-processing device that has been adapted to receive amplified electrical potential signals rather than electrical potentials that have yet to be amplified. Signal-processing device 18 may include, for example, a visual display for displaying the received amplified signals, a signal recorder component for recording the signal received for later review and analysis, and various signal-processing circuits and software for processing any amplified signals received. Such signal processing may include circuitry and software for further reducing any noise contained in the received amplified signals. In alternative embodiments, which are described in greater detail below, reference electrode module 12 and signal processing device 18 are adapted to assist an operator of system 10 to determine if an electrode 14 has been poorly affixed to subject 22.

Figure 2:
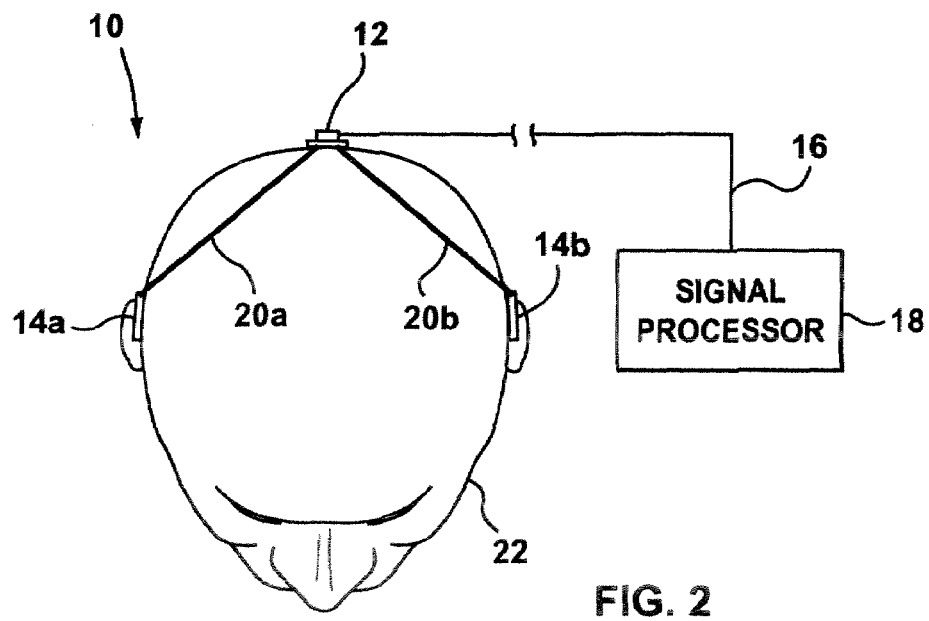
FIG. 2 is top view schematic diagram of the embodiment of FIG. 1.

Referencing FIG. 2, electrical potential system 10 is illustrated in a top view of subject 22. As noted above, lead wires 20a, 20b are tautly and electrically connect electrodes 14a, 14b to reference electrode module 12.

Figure 3:
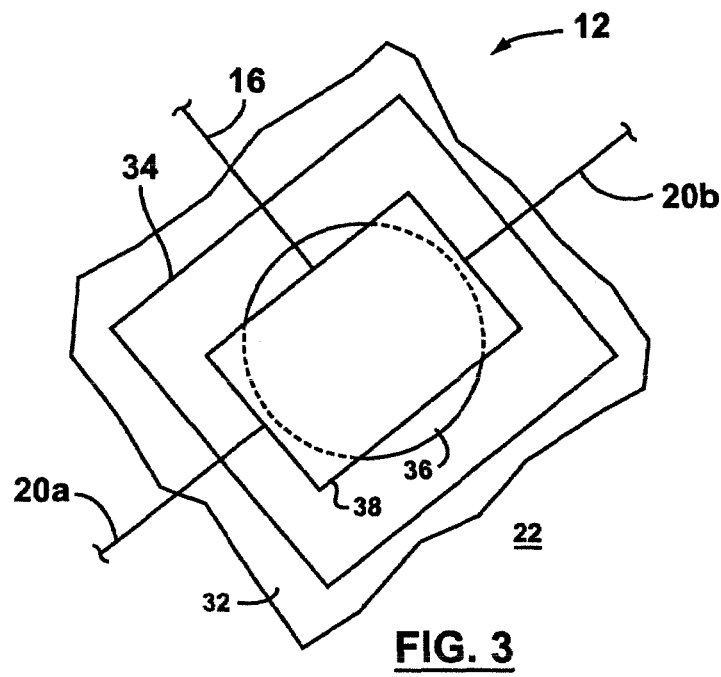
FIG. 3 is a schematic diagram of the reference electrode illustrated in FIGS. 1 and 2 embodying aspects of the present invention.

Reference electrode module 12 is illustrated in greater in FIG. 3. In the exemplary embodiment, reference electrode module 12 includes a conventional electrode that has been adapted to include amplifier component 38. Accordingly, reference electrode module 12 includes adhesive pad 34 that is used to affix electrode 12 to subject 22 and conductive pad 36 mounted to adhesive pad 34 for electrically connecting electrode 12 to subject 22.

In some embodiments reference electrode module 12 may include or be used in conjunction with a conventional conductive substance such as gel 32, for example, to assist in forming an electrical connection between the skin of subject 22 and conductive pad 36.

As known to those of ordinary skill in the art, conductive pad 36, which is typically composed of silver, silver-plated tin, silver-chloride, gold or other conductive materials, is adapted to provide an electrical connection between the subject 22 and, ultimately, signal processing device 18 (not shown in FIG. 3).

Electrically connected to conductive pad 36 is amplifier component 38. Amplifier component 38 is also adapted to be electrically connected to lead wires 20a, 20b and connector 16. Reference electrode module 12 also acts as the reference electrical ground for electrodes 14a and 14b.

Resulting from the inclusion of amplifier component 38 in reference electrode module 12, electrical potentials detected by electrodes 14 will be passed into amplifier component 38 for signal amplification. The use of short lead wires 20 (usually less than 15–20 cm in length on an adult human's head and even shorter on an infant's or small animal's head) results in far less noise being inductively or capacitively coupled to the lead wires that carries the signal from electrodes 14 to the amplifier component 38 than conventional electrode-lead and wire-amplifier arrangements. Additionally, since lead wires 20 are preferably taut, motion artifacts that induce noise in the lead wires 20 as they move through static (i.e., time invariant) electromagnetic fields are significantly reduced. The motion artifact noise is significantly reduced compared to known arrangements since lead wires 20a and 20b are likely to move through very similar paths and remain fixed relative to each other through these time-invariant electromagnetic fields. Consequently, there is likely to be only very small differential potentials resulting from these differential motion artifacts that will be detected by amplifier component 38.

Figure 4:
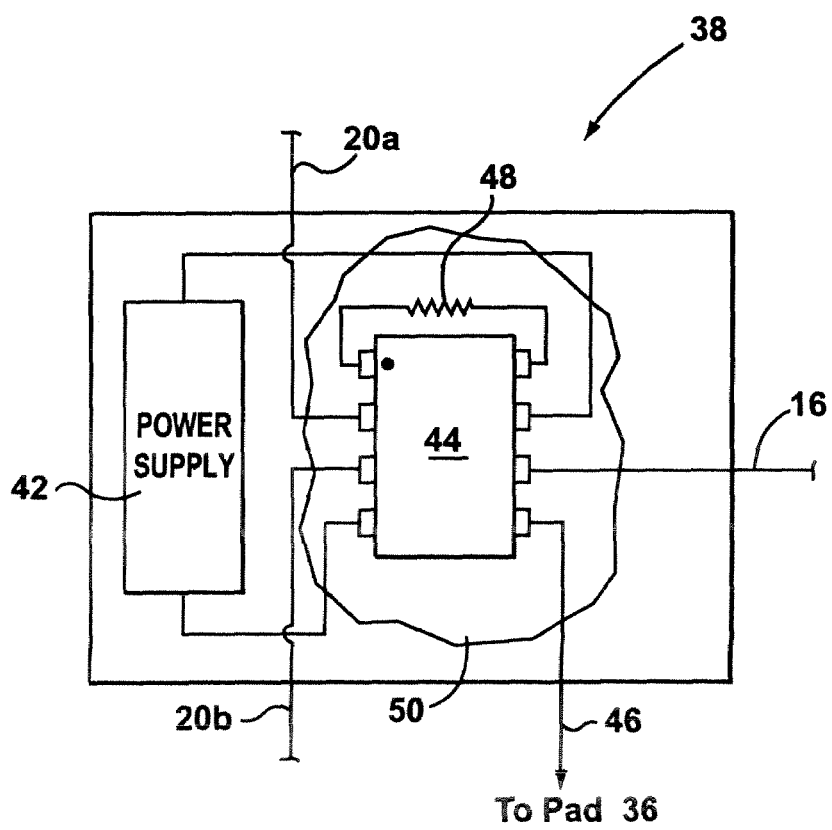
FIG. 4 is a more detailed diagram of the components of a portion of the reference electrode of FIG. 3.

A schematic of the elements included in amplifier component 38 is shown in detail in FIG. 4. Amplifier component 38 includes, in the present exemplary embodiment, a power supply 42, gain-setting resistor 48 and amplifier 44. Power supply 42 and gain-setting resistor 48 are both electrically connected to amplifier 44. Additionally, amplifier 44 is electrically connected to connector 16 (which also connects to signal-processing device 18—not shown in FIG. 4) and lead wires 20a and 20b (which are also electrically connected to electrodes 14a and 14b, respectively and not shown in FIG. 4). Amplifier component 38 may also include optional protective coating 50 to provide physical protection and additional electrical isolation of the various components. Epoxy or silicone resins known in the art may be appropriate for such a protective coating.

In the exemplary embodiment, amplifier 44 is an AD620 Instrumentation Amplifier available from Analog Devices of Norwood, Mass., USA (the data sheet for which is available from Analog Devices' web site at http://www.analog.com/UploadedFiles/Data_Sheets/37793330023930AD620_e.pdf, the contents of which are hereby incorporated herein by reference). Alternative embodiments may employ different amplifiers. For example, it is believed that the INA128 or INA129 amplifier from the Burr-Brown Corporation (part of Texas Instruments) of Tucson, Ariz., USA may be appropriate in some circumstances. As persons of ordinary skill in the art will appreciate, other amplifiers that could be employed in alternative embodiments will have different pin-outs resulting in slightly differing wiring from that illustrated in FIG. 4.

In the exemplary embodiment, the AD620 amplifier (amplifier 44) has its gain adjusted through use of different levels of resistance ($R_G$) between pins 1 and 8. A single resistor 48 connected between these pins can be used to set the level of gain (G) of amplifier 44. In the exemplary embodiment, gain is determined in accordance with equation (1) (where $R_I$ is internal resistance of amplifier 44 and is approximately 49.4 kΩ for the AD620 amplifier):

$$G = 1 + R_f/R_G \quad (1)$$

Resistor 48 may be a variable resistor or circuitry allowing for an operator to vary the level of resistance presented to amplifier 44 thus allowing for the modification of the level of gain applied to any differential potentials detected by amplifier 44. Typically, many operating environments will require a level of gain (G) exceeding 100 and preferably closer to 1000 (the maximum level of gain offered by the AD620 amplifier). Accordingly, resistor 48 would, in the exemplary embodiment, require a level of resistance between approximately 499.0 Ω and 49.5 Ω.

Power supply 42, which can be provided through use of a conventional (although preferably small) battery and any required and related circuitry known to those of ordinary skill in the art, is electrically connected to pins 4 and 6 of amplifier 44.

Lead wires 20a and 20b are electrically connected to pins 2 and 3 of amplifier 44.

Pin 8 of amplifier 44 is electrically connected to conductive pad 36 (FIG. 3) of reference electrode module 12. As a result of the electrical connection between amplifier 44 and conductive pad 36 (which, in turn, is connected to subject 22 during use), amplifier 44 will be provided with a reference electrical ground.

Referencing FIGS. 1–4, in operation of system 10, an operator affixes reference electrode module 12 and electrodes 14 to a subject in the relevant areas of interest in a manner known to those of ordinary skill in the art. The operator also electrically connects, by way of a lead wire 20, each electrode 14 to reference electrode module 12. In the exemplary embodiment, electrode 14a is connected to reference electrode module 12 by way of lead wire 20a and electrode 14b is connected to reference electrode module 12 by way of lead wire 20b. Lead wires 20 may be connected to electrodes 12, 14 prior or after fixation to the subject. As noted above, it is preferable that once electrodes 12, 14 have been affixed and lead wires 20 have been connected thereto, lead wires 20 are relatively taut. An operator also electrically connects reference electrode module 12 to signal processing device 18 by way of connector 16.

Amplifier 44, powered by power supply 42, will begin to detect differential electrical potential signals presented by electrodes 14a and 14b. Amplifier 44 then amplifies these detected signals by the set level of gain (G)—where, as noted above, the level of gain (G) is determined by resistor 48 and the inner components of amplifier 44. Since lead wires 20a, 20b connecting electrodes 14a, 14b to amplifier 44 are considerably shorter than the lead wires in known arrangements (i.e., 20 cm vs. 100–250 cm), the amount of electrical noise inductively or capacitively coupled to the lead wires is significantly reduced. Accordingly, amplifier 44 is presented with electrical signals having a much greater (i.e., improved) signal to noise ratio than in known arrangements. Additionally, since lead wires 20a, 20b are substantially fixed relative to each other (especially, if lead wires 20a and 20b are taut), motion artifacts created by the movement of lead wires along different physical paths through electromagnetic fields (a source of considerable noise in known systems) are also significantly reduced.

Once electrical potentials detected by amplifier 44 have been amplified (resulting in an amplified signal having considerably less noise than known systems), the amplified signal is transmitted to signal processing device 18 via connector 16. The amplified signal can then be further processed, recorded and analysed to provide the required diagnostic test being performed on subject 22.

As will be appreciated by those of ordinary skill in the art, the resulting significant reduction in noise presented to the amplifier of system 10 results in a reduction of signal processing that needs to be performed to eliminate or reduce noise in any signal detected as compared to known systems. Consequently, time averaging techniques which are presently employed to reduce the effects of noise in a detected signal and which require multiple and/or lengthy tests to be conducted may be reduced in many cases.

Figure 5:
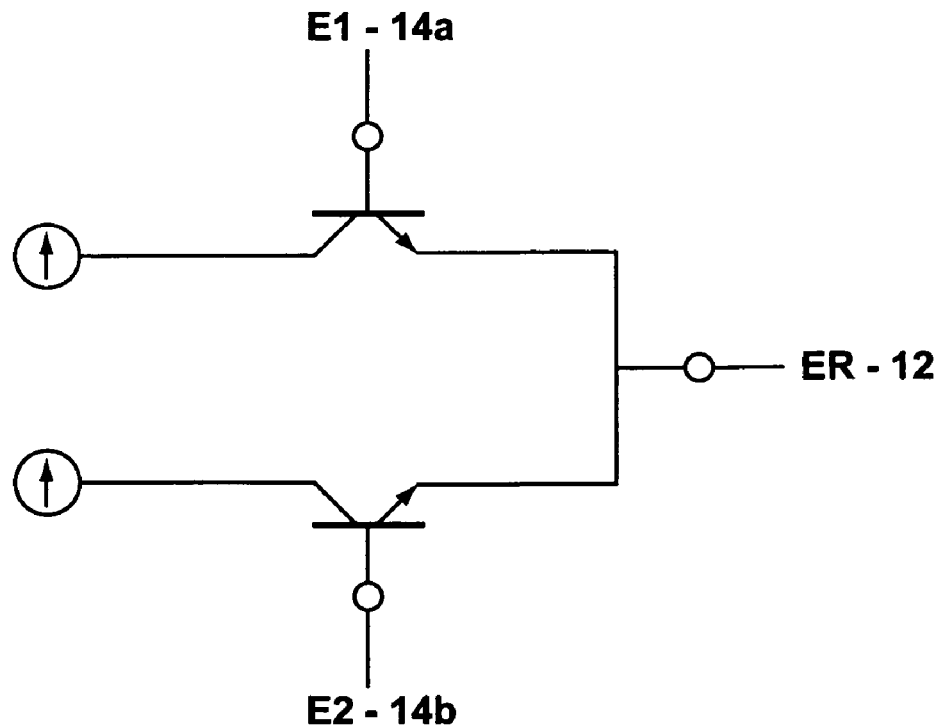
FIGS. 5 and 6 are simplified circuit diagrams of the reference electrode illustrated in FIG. 3.
Figure 6:
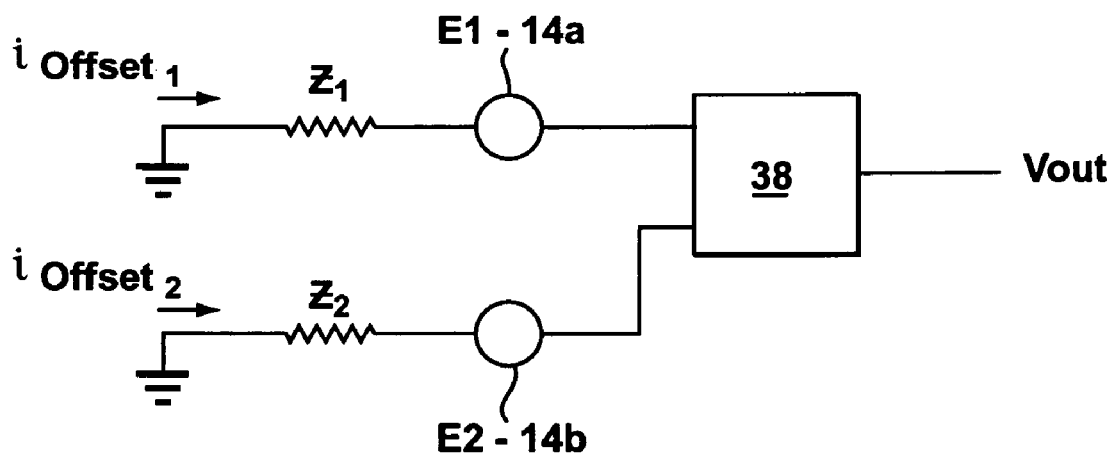

An exemplary simplified circuit diagram for system 10 is illustrated in FIGS. 5 and 6. Resulting from the arrangement and the selection of the components therein, system 10 can also be used to assist in determining if one of electrodes 14a or 14b, has become detached from subject 22 and, if so, provide assistance in determining which one of the electrodes has become so detached. System 10 includes an impedance detection that may be used whenever an amplifier with bipolar transistor inputs (e.g., the AD620 amplifier described above) is used to detect the signal (i.e., the electrical potential generated by the subject). As those of ordinary skill in the art will appreciate, a bipolar transistor amplifier will introduce an input bias current into each of the differential signal inputs. These bias currents are an inherent property of the bipolar transistor inputs and result in an offset at the amplifier output that is proportional to the difference in impedance between the input leads (e.g., the impedance presented by the lead wire-electrode-subject arrangement). Adapting signal-processing device 18 to determine the polarity or phase of the common-mode signal, signal-processing device 18 can be used to determine which electrode contact is faulty thus reducing the time-consuming and painstaking process that afflicts current electrode arrangements. An operator would then be presented with some form of sensory feedback or signal indicating which one of the electrodes 14 has a faulty or poor connection to subject 22. The sensory feedback presented to the operator may be one or more of the following: a visual signal or indicator (e.g., a text and/or graphical message), an audible signal (e.g., a warning buzzer with, for example, different tones and/or volumes to indicate which electrode has a poor/faulty connection), and/or a tactile or other sense of touch signal (e.g., a vibration generated by a device—such as, for example, a pager-like device—worn by operator, with different types of vibrations associated with each of electrodes 14). In the preferred embodiment, the sensory signal is a combination of an audible alarm or warning coupled with a visual signal output on a display screen forming part of signal-processing device 18. The audible alarm provides an indication that one of the electrodes 14 has a poor or faulty connection to subject 22 and prompts the operator to review the display screen of signal-processing device 18. The visual indicator displayed by signal-processing device 18 provides to the operator data (text and/or graphics) indicating which one of the electrodes 14 is the source of the problem.

Referring to FIG. 6, $Z_1$ represents the impedance presented to amplifier 44 by the connection between the subject 22 and electrode 14a and $Z_2$ represents the impedance presented to amplifier 44 by the connection between subject 22 and electrode 14b. The bias current flowing through the subject-electrode connections is represented by $i_{offset1}$ and $i_{offset2}$, respectively. The offset voltage ($V_{offset}$) follows equation (2) set out below:

$$((i_{offset1} - i_{offset2})(Z_1 - Z_2)G) = V_{offset} \quad (2)$$

If the impedances of the subject-electrode connections are the same or similar (i.e., both are well adhered or affixed to the subject) the second term of equation (2) will be zero or very small resulting in a very small offset voltage. If one of the two electrodes is poorly affixed to subject 22 (or has become disconnected), then the offset voltage will be relatively large. If electrode 14a is disconnected $V_{offset}$ will be much greater than zero and this value can be displayed (or some other signal generated) to an operator of system 10 by signal processing device 18. Consequently, the operator of system 10 will be provided information identifying the electrode which has been poorly connected or affixed to subject 22 saving considerable time and effort that would otherwise be expended. Similarly, if $V_{offset}$ is much less than zero, this value is indicative of electrode 14b being disconnected or poorly connected to subject 22 and the operator can be informed of this situation. As a result of this operation of system 10, an operator of system 10 can spend much less time making a determination of which of the electrodes needs to be re-attached or better attached to subject 22.

As will be appreciated, in alternative embodiments of the present invention having multiple pairs of electrodes 14 affixed to a subject, the assistance provided to an operator of system 10 in determining which electrodes 14 have been poorly attached to the subject will result in significant time and cost savings.

This advantage of the present invention is suitable for applications where the signal of interest is a differential signal. Beneficially, such an advantage requires no additional circuitry to generate, filter and detect the impedance signal and results in a reduction of the cost, size, complexity, and total noise of the system compared current arrangements. A further advantage of the impedance detection method and apparatus is that it is particularly well suited for use in a small space; the type of physical environment in which electrodes are often employed.

Some alternatives to the exemplary embodiment illustrated as system 10 will now be described.

Figure 7:
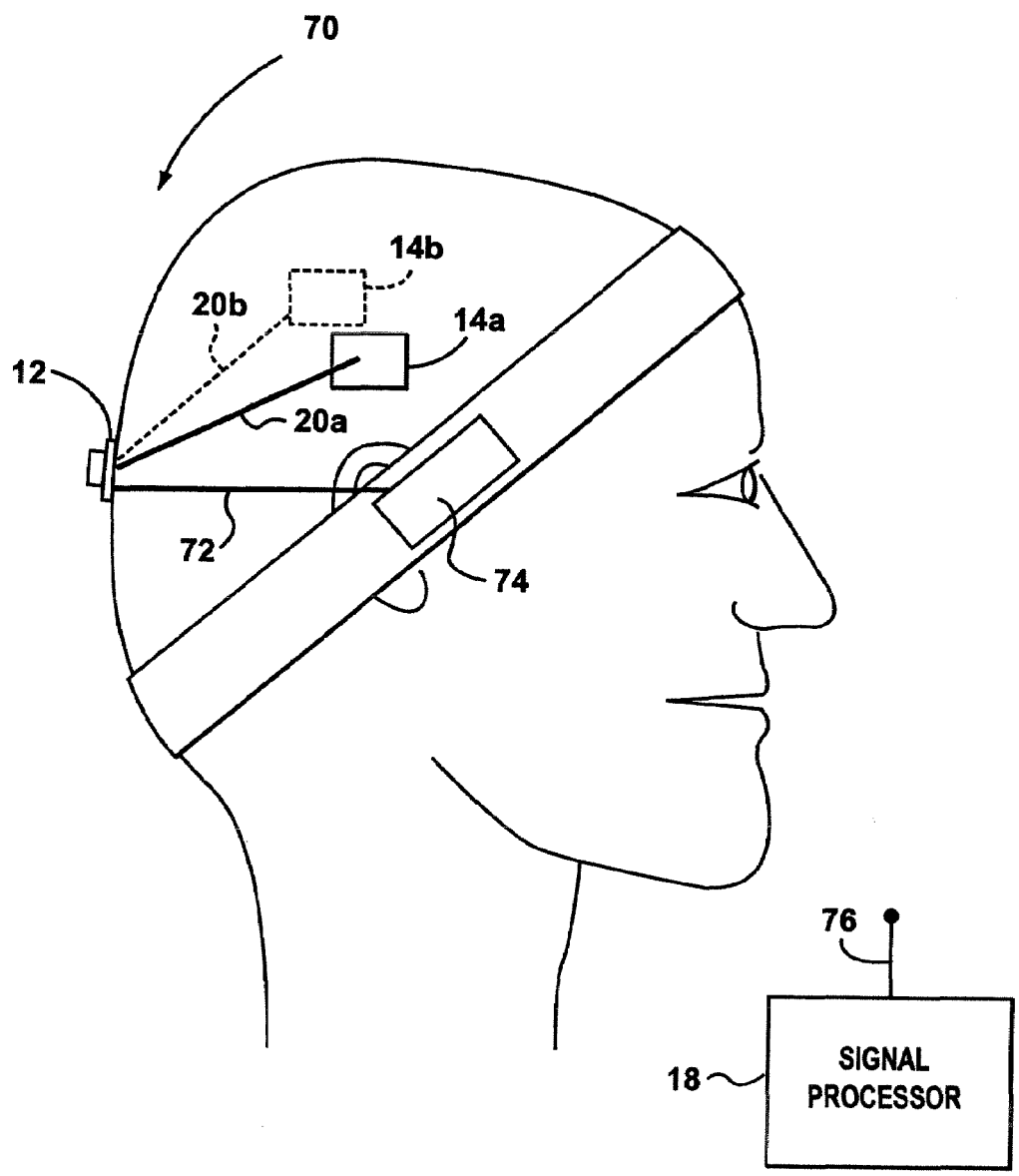
FIG. 7 is a side view schematic of an alternative embodiment of the present invention affixed to a subject's (human's) head.

In one alternative embodiment, system 10 is adapted to transmit amplified signals from the subject to signal processing device 18 using a wireless connection as illustrated by system 70 in FIG. 7. Similar to system 10 (FIG. 1), system 70 includes a pair of conventional electrodes 14a, 14b electrically connected by way of lead wires 20a, 20b, respectively, to reference electrode module 12. Reference electrode module 12, which also includes the amplifier component 38 described above, is electrically connected to connector 72 rather than connector 16. Connector 72 electrically connects reference electrode module 12 to signal transmitter 74.

Signal transmitter 74 is adapted to receive the detected and amplified signals (as described above) processed by amplifier component mounted to reference electrode module 12. However, rather than transmit the detected and amplified signal over a wire to signal-processing device 18 like system 10 of FIG. 1, signal transmitter 74 transmits the signal via radio waves to signal-processing device 18. In turn, signal processing device 18 has been adapted to receive the transmitted radio signal by inclusion of radio-receiving device and antenna 76. Those of ordinary skill in the art will appreciate that signal transmitter 74 will modulate (either in the amplitude or frequency domains, or both) a radio signal of selected frequency and, thus, will include circuitry and power sources (e.g., a battery) to perform this function. Additionally, signal transmitter 74 may include some filtering circuitry to remove some of the unwanted (although limited) noise included in the amplified signal generated by reference electrode module 12.

In a further alternative, signal transmitter 74 may transmit a digital representation of the amplified signal generated by reference electrode module 12. In this alternative embodiment, signal transmitter would include a conventional analog-to-digital processor (A/D). The digital representation could then be transmitted using known wireless transmission protocols (e.g., BlueTooth, 802.11a, b or g, or the like). In this instance, receiving device and antenna 76 would also require some modification so that the digitally transmitted signal can be received and processed as required.

While the preferred embodiment includes the amplifier component mounted directly on the underlying electrode, a further alternative embodiment includes the amplifier component affixed to subject 22 and near to the underlying electrode (i.e., near to conductive pad 36 of reference electrode module 12). For example, amplifier component could be included in the circuitry of signal transmitter 74 (FIG. 7).

In a still further alternative embodiment, the amplifier component is mounted on or near a signal electrode (rather than mounting the amplifier component on or near the reference electrode) to form an electrode module.

In view of the many possible embodiments to which the principles of this invention may be applied, it should be recognized that the embodiments described herein and shown in the drawing figures is meant to be illustrative only and should not be taken as limiting the scope of invention. For example, those of skill in the art will recognize that the elements of the illustrated embodiment can be modified in arrangement and detail without departing from the spirit of the invention. Therefore, the invention as described herein contemplates all such embodiments as may come within the scope of the following claims and equivalents thereof.

The invention claimed is:

1. An electrode module for affixing to a subject to assist in measuring electrical potentials in said subject, said electrode module comprising a differential amplifier component mounted directly to and in electrical contact with an electrode that is to be used as a ground electrode and said amplifier component having inputs for electrical potentials from two or more signal electrodes and said amplifier component is configured to amplify only the difference in electrical potential between pairs of said two or more signal electrodes,
   wherein said two or more signal electrodes comprise a first signal electrode and a second signal electrode and wherein said amplifier is further adapted to, when one of said first or said second signal electrode is poorly connected to, or detached from, a subject, transmit a signal indicating which of said first or said second signal electrode is poorly connected to, or detached from, said subject.

2. The electrode module of claim 1 wherein said amplifier component further comprises a wireless signal transmitter, said wireless signal transmitter adapted to wirelessly transmit said amplified differential signal to a signal-processing device.

3. The electrode module of claim 2 further comprising filter circuitry for filtering electrical signals received from said two or more signal electrodes.

4. The electrode module of claim 3 wherein said filter circuitry filters said amplified electrical signal.

5. The electrode module of claim 2 wherein said wireless signal transmitter is adapted to transmit a digital representation of said amplified electrical signal to a signal-processing device.

6. The electrode module of claim 1 wherein said amplifier comprises bipolar transistor inputs.

7. The electrode module of claim 1 wherein said amplifier comprises a bipolar transistor amplifier, said bipolar transistor amplifier introducing a bias current into the signals received from said first and second signal electrodes.

8. The electrode module of claim 7 wherein said bipolar transistor amplifier generates an output proportional to the difference between the impedance presented to said bipolar transistor amplifier by said first and second signal electrodes; and wherein said signal indicating which of said first or said second signal electrode is poorly connected to, or detached from, said subject comprises a signal based upon said output proportional to the difference in impedance presented to said bipolar transistor amplifier.

9. The electrode module of claim 8 wherein said signal indicating which of said first or said second signal electrode is poorly connected to, or detached from, said subject comprises at least one of a visual signal, an audible signal and a tactile signal, said signal for presentation to an operator by a signal processing device.

10. The electrode module of claim 1 wherein said signal indicating which of said first or said second signal electrode is poorly connected to, or detached from, said subject comprises a sensory signal for presentation to an operator.

11. The electrode module of claim 1 wherein said amplifier is adapted to be removably mounted directly to said ground electrode.

12. A method of amplifying electrical potentials in a subject, said method comprising:
    placing a plurality of electrodes on the subject, wherein one of said plurality of electrodes is a ground electrode having a differential amplifier mounted thereon and the remainder of said plurality of electrodes are signal electrodes;
    electrically connecting said differential amplifier with a pair of said plurality of electrodes;
    amplifying the difference in electrical potential received from said pair of signal electrodes; and
    detecting if one of said pair of signal electrodes is poorly affixed to, or detached from, a subject and, if so, presenting to an operator a sensory signal indicating which one of said signal electrodes is poorly affixed to, or detached from, said subject.

13. The method of claim 12 further comprising transmitting said amplified differential electrical potential signal to a signal-processing device.

14. The method of claim 12 further comprising transmitting said amplified differential electrical potential signal to a signal-processing device via a wireless connection.

15. The method of claim 14 wherein said transmitting comprises generating a modulated radio frequency signal representative of said amplified differential electrical potential signal.

16. The method of claim 14 further comprising, prior to said transmitting, generating a digital representation of said amplified differential electrical potential signal.

17. The method of claim 12 wherein said sensory signal comprises at least one of: a visual signal; an audible signal; and a tactile signal.

18. The method of claim 12 wherein said presenting to an operator a sensory signal comprises generating said sensory signal responsive to the difference in impedance presented by said signal electrodes to said amplifier.

19. The method of claim 18 wherein said generating comprises introducing a bias current into said inputs received from said pair of signal electrodes.

20. The method of claim 18 wherein said amplifier comprises a bipolar transistor amplifier.

21. A system for measuring electrical potentials in a subject, said system comprising:
    a plurality of electrodes comprising at least one electrode acting as a reference ground electrode and at least one pair of electrodes acting as signal electrodes;
    a differential amplifier mounted to said reference electrode, said reference electrode comprising a conductive pad electrically connected to said amplifier, said amplifier having inputs for signals from said at least one pair of signal electrodes and configured for amplifying a differential electrical signal detected by said pair of signal electrodes,
    wherein, in the event that one of said pair of electrodes is poorly affixed to, or detached from a subject, said amplifier adapted to generate a signal indicating which one of said pair of electrodes is poorly affixed to, or detached from, said subject.

22. The system of claim 21 wherein said amplifier comprises a bipolar transistor amplifier.

23. The system of claim 21 wherein said signal indicating which one of said pair of electrodes is poorly affixed to, or detached from, said subject comprises a sensory signal for presentation to an operator, said sensory signal comprising at least one of: a visual signal; an audible signal; and a tactile signal.

24. The system of claim 21 further comprising a connector electrically connecting an output of said amplifier to a signal-processing device.

25. The system of claim 24 wherein said connector comprises a wireless transmitter for wirelessly transmitting the output of said amplifier to a signal-processing device.

26. The system of claim 25 wherein said wireless transmitter further comprises an analog-to-digital converter for generating a digital representation of the output of said amplifier and wherein said wireless transmitter transmits said digital representation to a signal-processing device.

27. The system of claim 21 further comprising filtering circuitry, said filtering circuitry adapted to filter out noise from said differential electrical signal detected by said electrodes.

28. The system of claim 27 further comprising filtering circuitry, said filtering circuitry adapted to filter out noise from said amplified differential electrical signal detected by said electrodes.

* * * * *